United States Patent
Chodór

(10) Patent No.: US 11,185,407 B2
(45) Date of Patent: Nov. 30, 2021

(54) STENT OF AORTIC VALVE IMPLANTED TRANSCATHETERLY

(71) Applicant: Piotr Chodór, Zernica (PL)

(72) Inventor: Piotr Chodór, Zernica (PL)

(*) Notice: Subject to any disclaimer, the term of this patent is extended or adjusted under 35 U.S.C. 154(b) by 69 days.

(21) Appl. No.: 16/343,684

(22) PCT Filed: Oct. 18, 2017

(86) PCT No.: PCT/PL2017/000105
§ 371 (c)(1),
(2) Date: Apr. 19, 2019

(87) PCT Pub. No.: WO2018/080328
PCT Pub. Date: May 3, 2018

(65) Prior Publication Data
US 2019/0240006 A1  Aug. 8, 2019

(30) Foreign Application Priority Data

Oct. 19, 2016 (PL) .......................................... 419173
Oct. 18, 2017 (PL) .......................................... 423186

(51) Int. Cl.
A61F 2/24    (2006.01)
A61F 2/91    (2013.01)

(52) U.S. Cl.
CPC ............ *A61F 2/2418* (2013.01); *A61F 2/91* (2013.01); *A61F 2210/0014* (2013.01); *A61F 2230/0013* (2013.01); *A61F 2250/0098* (2013.01)

(58) Field of Classification Search
CPC ......... A61F 2/24; A61F 2/2412; A61F 2/2418
(Continued)

(56) References Cited

U.S. PATENT DOCUMENTS

2005/0234546 A1   10/2005  Nugent et al.
2008/0255660 A1*  10/2008  Guyenot ............... A61F 2/2442
                                                    623/2.14
(Continued)

FOREIGN PATENT DOCUMENTS

DE    212013000104       11/2014
EP        2520249 A1     11/2012
(Continued)

OTHER PUBLICATIONS

Hangzhou, Venus MEDECH Artificial hear valve and its flap holder DE212013000104U1 (Year: 2012).*
(Continued)

*Primary Examiner* — Suzette J Gherbi
(74) *Attorney, Agent, or Firm* — Horst M. Kasper, Esq.

(57) ABSTRACT

The invention describes a stent of the aortic valve which is self-expandable and also repositionable and preferably made from nitinol. It consists of two parts: the upper part and the lower part. The lower part is a mesh (1) laid out so that it creates a kind of cylinder wall on the entire height of the element. Also other shape of the mesh is acceptable, for example partially conical, or partially resembling flattened side wall of the cylinder. However, the upper part of the stent consists of derived from the mesh (1) upwards and arranged at equal intervals three arms (2) the height of which is slightly larger than the height of the mesh (1), a bit less than the height of the mesh (1) or equal to its height. The stent arms (2) are shaped in such a way that they form together a kind of an oval chalice bowl, and their end, peripheral part is preferably straight and also inclined to the middle. Space between the arms (2) always ensures free access to patient's coronary arteries. At the end of each of the arms (2) is an upper tag (3) of the valve and each upper tag (3) has its corresponding lower tag (8) located at the bottom of the mesh (1) which is on the opposite side and below a given (Continued)

Figure 1:
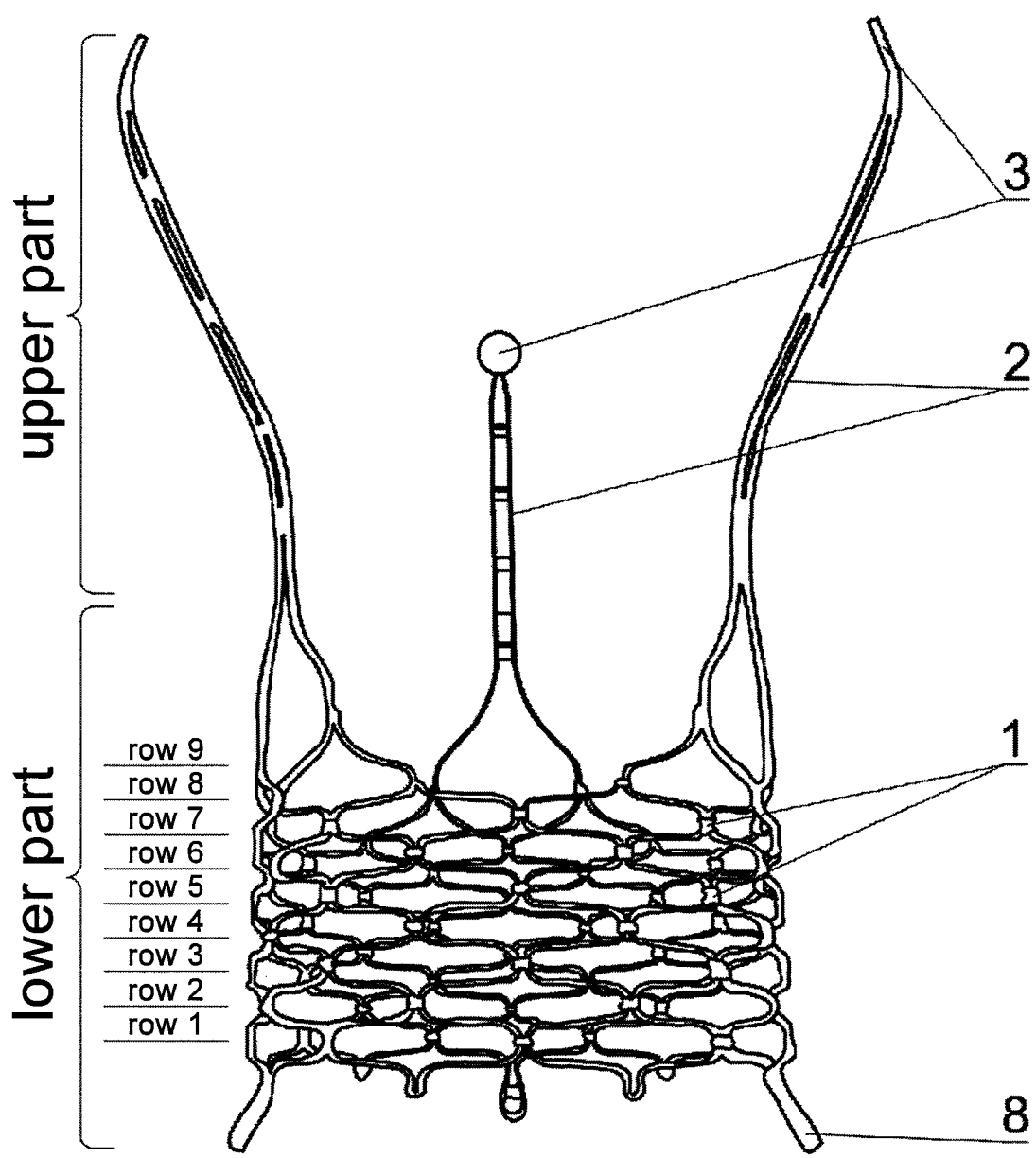

arm (2). The lower valve tag (8) enables precise implantation of the stent according to scheduled plan.

5 Claims, 6 Drawing Sheets

(58) Field of Classification Search
USPC .................................................. 623/2.1–2.18
See application file for complete search history.

(56) References Cited

U.S. PATENT DOCUMENTS

| | | | |
|---|---|---|---|
| 2009/0216312 A1 | 8/2009 | Straubinger et al. | |
| 2010/0191320 A1* | 7/2010 | Straubinger | A61F 2/2418 |
| | | | 623/1.15 |
| 2010/0256723 A1* | 10/2010 | Murray | A61F 2/2418 |
| | | | 623/1.2 |
| 2012/0271398 A1 | 10/2012 | Essinger et al. | |
| 2014/0018935 A1* | 1/2014 | Wang | A61F 2/2409 |
| | | | 623/23.68 |
| 2014/0249622 A1* | 9/2014 | Carmi | A61F 2/2436 |
| | | | 623/2.11 |
| 2014/0277390 A1* | 9/2014 | Ratz | A61F 2/2418 |
| | | | 623/1.26 |
| 2015/0265402 A1 | 9/2015 | Centola et al. | |
| 2015/0351903 A1* | 12/2015 | Morriss | A61F 2/2418 |
| | | | 623/2.11 |
| 2016/0158007 A1 | 6/2016 | Centola et al. | |
| 2016/0213465 A1 | 7/2016 | Girard et al. | |
| 2017/0281341 A1* | 10/2017 | Lim | A61F 2/2418 |
| 2018/0168803 A1* | 6/2018 | Pesce | A61F 2/2409 |
| 2019/0046701 A1* | 2/2019 | Kallenbach | A61M 60/857 |
| 2019/0083263 A1* | 3/2019 | Hariton | A61F 2/243 |
| 2019/0388225 A1* | 12/2019 | Perszyk | A61F 2/848 |
| 2020/0054449 A1* | 2/2020 | Min | A61F 2/2457 |
| 2020/0170814 A1* | 6/2020 | Neilan | A61L 31/08 |
| 2020/0246142 A1* | 8/2020 | Rothstein | A61F 2/2418 |

FOREIGN PATENT DOCUMENTS

| | | |
|---|---|---|
| EP | 2959866 A1 | 12/2015 |
| EP | 3028668 A1 | 6/2016 |
| WO | 2009053497 A1 | 4/2009 |
| WO | 2006124649 A2 | 11/2009 |

OTHER PUBLICATIONS

Willson, AB et al. Transcatheter Aortic Valve Replacement With the St. Jude Medical Portico Valve: First-In-Human Experience, Journal of the American College of Cardiology, Aug. 14, 2012, vol. 60, No. 7, 2012; pp. 581-586.

\* cited by examiner

STENT OF AORTIC VALVE IMPLANTED TRANSCATHETERLY

The subject of the invention is a stent of aortic valve, implemented transcatheterly.

Human aortic valve is between the left ventricle of the heart and ascending aorta, i.e. the first part of the aorta. It provides a unidirectional flow of blood from the left ventricle of the heart to the aorta, which is the starting point of the systemic circulation. The valve opens at time of a contraction of the left ventricle of the heart, when the pressure in the left ventricle exceeds the aorta pressure. Whereas in the period of a diastole of the left ventricle, when the pressure in the left ventricle drops below the aorta pressure—the valve closes automatically.

Traditionally, a recognized treatment modality of aortic valve stenosis is surgical replacement of the aortic valve with an artificial or biological valve. This is a method known for more than 40 years and according to the guidelines of the European Society of Cardiology is within the first class of indications. Unfortunately, this method is associated with the necessity of surgical opening of the chest (sternotomy) and the application of cardiopulmonary bypass. The data published by the Society show that at the beginning of the 21st century one third of patients diagnosed with aortic valve stenosis was not operated on. The reason for this is the fact that the disease is now especially present in older population of patients in the 6th, 7th, 8th, 9th decade of life. This age group very frequently suffers from comorbidities. The patients are not receiving surgical treatment because of recognition of severe comorbidities, high surgical risk or inoperability. In 2002 Alan Cribier was first to implant an aortic valve to a patient without opening the chest and the necessity to connect cardiopulmonary bypass. This was the method currently referred to as "TAVI" (TRANSCATHETER AORTIC VALVE IMPLANTATION). The valve implanted by prof. Cribier was a valve referred to as "Cribier-Edwards" valve. It was actually a bovine valve on metal stent, implanted through the expansion of a balloon on which it was mounted. Currently the third generation of transcatheterly implanted valves is in use: "Sapien 3". This valve consists of a cobaltic and chromic alloy scaffold and bovine pericardium. After the implantation it mostly provides access to the coronary arteries and allows performance of coronarography. Nevertheless, this possibility depends on the height of the executed implantation. This valve cannot be repositioned, which means that once implanted, it cannot be reimplanted or moved.

Then, a valve called "Core Valve" was placed on the market. Currently newer versions of this valve are available, marked "Evolut R" and "Evolut R Pro". These are valves implementing a completely different concept of transcatheterly implanted valves. They are made of nitinol and are self-expandable. Additionally, "Evolut R" and "Evolut R Pro" valves can be repositioned, i.e. they can be folded in the patient's body—in case of improper implantation—and reimplanted. Valve repositioning is done in cases where the valve has not yet been disconnected from the delivery system, but is already working. At this point you can check and make sure that it is properly located and you can decide about its ultimate disconnection from the delivery system and thus about the final implantation. Leaflets of this biological valve are made of porcine pericardium. Generally, however, this valve hinders the access to the coronary arteries due to the crown of nitinol in the shape of a fairly dense mesh. This valve is implanted also in the way which does not provide sufficient and secure location of new valve leaflets opposite the semilunar leaflets of the patient's aortic valve. A biological valve of this design is according to the assumption sewn into the stent supra-annularly—i.e. few millimeters over the patient's aortic valve annulus.

Another valve, "Portico" is also a nitinol valve, self-expandable, possible to be repositioned, with a biological valve implanted at the height of the annulus of aortic valve. Its leaflets are made of bovine pericardium. However, it prevents the free access to the coronary arteries. This valve is implanted also in the way which does not provide sufficient and secure orientation of the new valve leaflets opposite the semilunar leaflets of the patient's aortic valve.

Another valve implanted using the "TAVI" method is "BioValve". It is currently under examination. The first reports of its implantation in humans have appeared. It is also a nitolin valve, self-expandable and possible to be repositioned. Likewise, however, its design does not provide free access to the coronary arteries. It is also implanted in the way which does not provide sufficient and secure orientation of the new valve leaflets opposite the semilunar leaflets of the patient's aortic valve. Leaflets of this biological valve are made of porcine pericardium.

A different aortic valve to be implanted using the "TAVI" method is "Accurate" valve. This is a valve in which the biological valve leaflets are made also of porcine pericardium. It is a nitinol, self-expandable valve, but it cannot be repositioned. You cannot change its position in the event of an abnormal implantation. Although it provides easy access to the coronary arteries, but in practice a precise implementation is also a requirement for such a possibility. And indeed, too high implantation does not allow free access to the coronary arteries, and it happens in clinical practice. Then, unfortunately, you cannot improve its position. The valve is implanted in the way which does not provide sufficient and secure orientation of the new valve leaflets opposite the semilunar leaflets of the patient's aortic valve.

In recent times, many new valves appeared with different, original designs, such as "Direct Flow" valve which is constructed of metal-free polyester scaffolding. Its leaflets are made also of bovine pericardium. This valve provides access to the coronary arteries, can be repositioned and is implanted in an original way.

The next known valve is "Lotus" valve. This is actually a nitinol, self-expandable, implanted in an original way valve. Its leaflets are made of bovine pericardium. The valve theoretically provides access to the coronary arteries and can be repositioned. Its shape and method of implantation is quite different from other self-expandable valves such as "Core Valve", "Evolut R", "Portico" and "BioValve".

From the American description of the invention with the application number US2014163667 is known a solution entitled "Stentless aortic valve replacement with high radial strength". A stentless, intravascularly implanted heart valve is presented there. The valve formed at the place of implantation shows excellent resistance to crushing compared to conventional valves expanded using a balloon or based on a self-expandable stent.

From the Japanese description of the invention with the application number JP2014000417 is known a similar solution entitled "Transluminally implantable heart valve with formed in-place support". The invention solves the problem of a need to resign from the stent and deliver the valve in place of implantation without the help of other structures. The developed prosthetic heart valve includes: filled cuff with at least one channel that is configured so as to create a construction that is at least partially filled. The valve is designed so that it allows the flow in one axial direction, and blocks the flow in the other axial direction, the opposite in relation to the first. The valve consists of many tissular elements which constitute its reinforcement.

From another, Polish description of the invention with the application number P-293772 (BUP date of publication 1993 Sep. 20) is known a solution entitled "Flexible stent for heart valve". This stent is composed of plastic bearing element forming a homogenous structure, collar and hem material made of a homogenous piece without cuts, uniformly tight over the entire surface of the stent. Plastic bearing element has the shape of a truncated cone or similar to a truncated cone with an apical angle at most equal to 8°. Three spread supporting arms have the top radius which is at most ⅛ of the diameter of the bearing element at the base. On a flat base of the bearing element there are three indentations in the axis of supporting arms with radii equal to at most twice the top radius of the supporting arm and a height of 1 mm. The internal diameter of the element measured at the base depends on the size of the used valve and ranges from 17 to 33 mm. A stent is a structural component that allows the implantation of natural animal and human valves, and, in particular, human pulmonary valve in mitral and tricuspid position.

The purpose of the invention is the development of a heart valve stent, as well as improved versions of such stent which will connect the advantages of previously known designs, and will allow the creation of a valve which is self-expandable and can be repositioned, however, it is affixed better than those previously known and allows access to the patient's coronary arteries after implantation, and allows its accurate and planned positioning during implantation operation.

Has been developed a stent of aortic valve that has three arms in the upper part and is self-expandable and can be repositioned and consists of two parts: the upper part and the lower part. Wherein the lower part consists of a mesh laid out so that it creates a kind of peripheral wall of this element. However, the upper part of the stent consists of derived from the mesh upwards and arranged at equal intervals three arms the height of which is slightly larger than the height of the mesh, a bit less than the height of the mesh or equal to its height. The essence of the developed stent lies in that the end, peripheral part of its arms usually is straight or curved inwards or inclined to the outside and at the same time whole arms are:
  S-shaped or
  C-shaped or
  straight and
at the same time are:
  pointed straight up or
  inclined to the middle or
  inclined outwards,
wherein space between the arms ensures free access to patient's coronary arteries. However, at the end of each arm an upper valve tag is placed, and each upper tag has its corresponding tag located at the bottom of the mesh, which is on the opposite side of the given arm. Each lower tag is different from others and can be seen with X-rays, allowing planned and precise implantation of the valve, and peripheral wall of the mesh is cylindrically shaped or almost cylindrically shaped, preferably at least partially funnel-shaped and hourglass-shaped.

Preferably, in the developed stent of aortic valve at least its mesh is made of material showing so-called "shape memory effect", preferably of nickel and titanium alloy, optimally from nitinol and/or made from wire, or constitutes a monolithic element preferably made from tube.

Preferably, the arm of the developed stent has a single or double structure, i.e. it consists of a single boom or two juxtaposed with each other, possibly integrated and at least partly adjacent to each other.

Preferably, the upper valve tag resembles in shape a spherical disk or small, low, almost flat cylinder with rounded edges or has a shape of flat element of unique shape or is derived from the arm and constitutes its curvature and additionally, possibly has characteristic holes or patterns.

Preferably, the mesh has at least two, preferably three or nine rows of mesh holes, wherein preferably the holes have the shape similar to the contour of longitudinal section of a lemon or have the shape similar to the contour of a drop.

Figure 2:
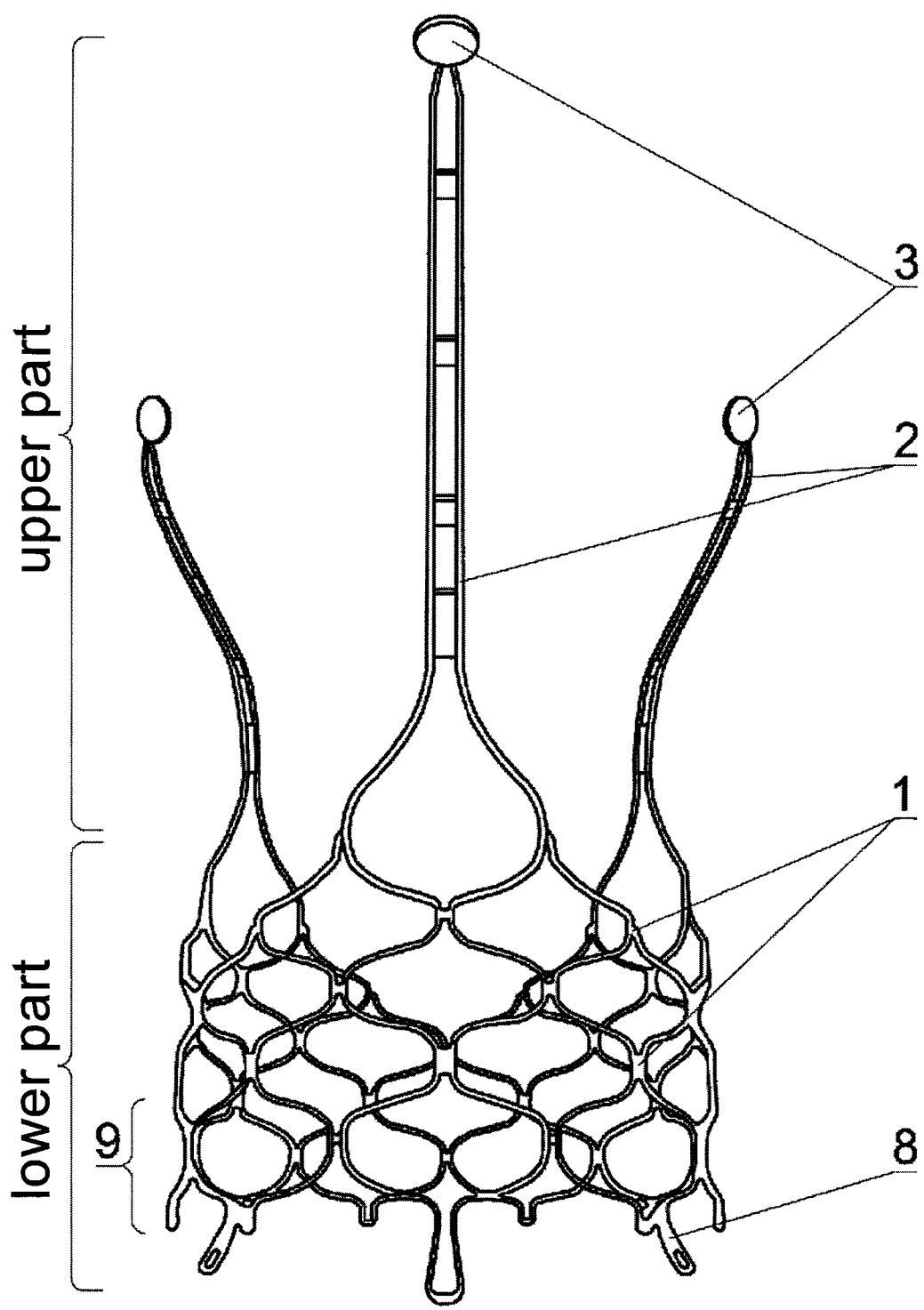
Figure 3:
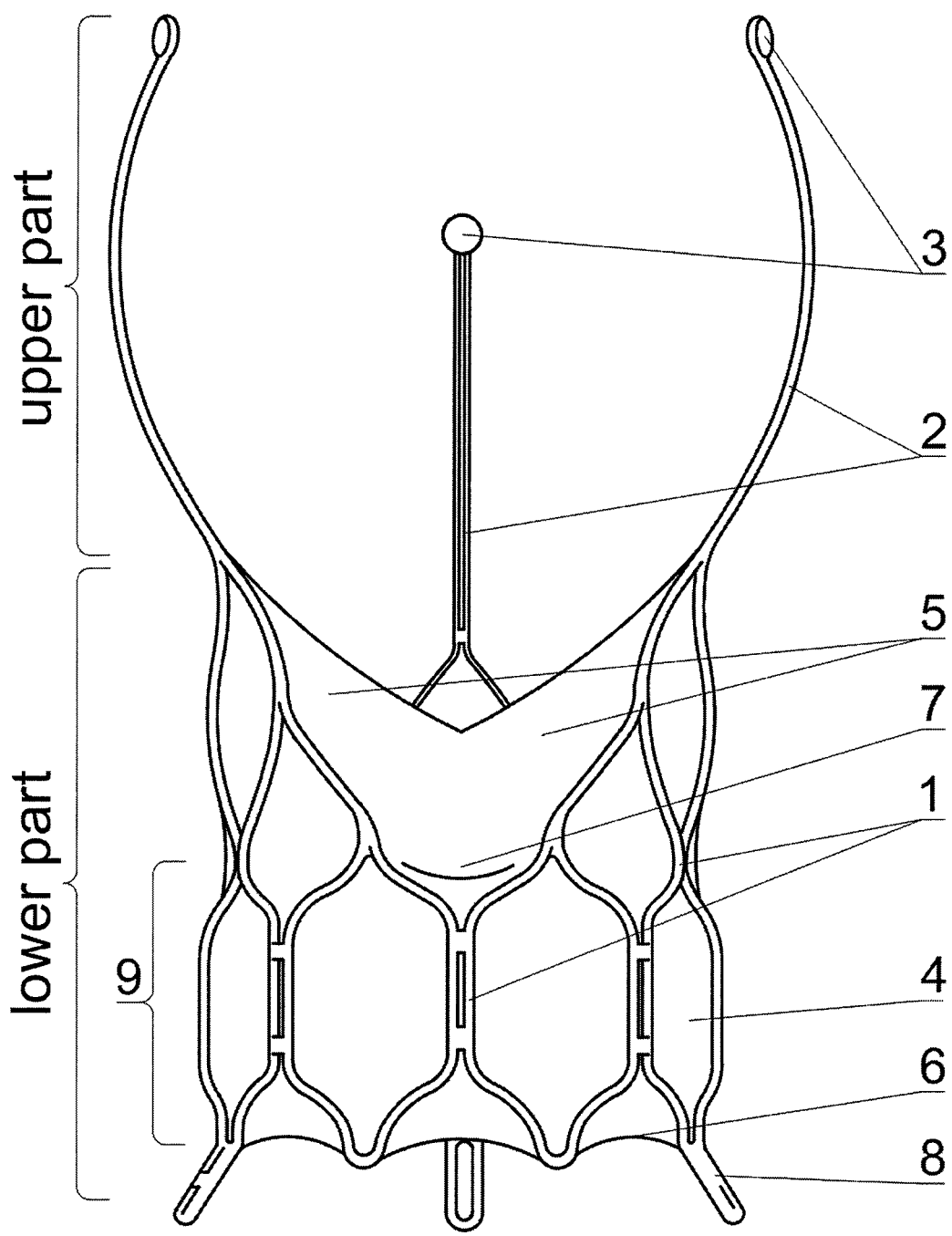
Figure 4:
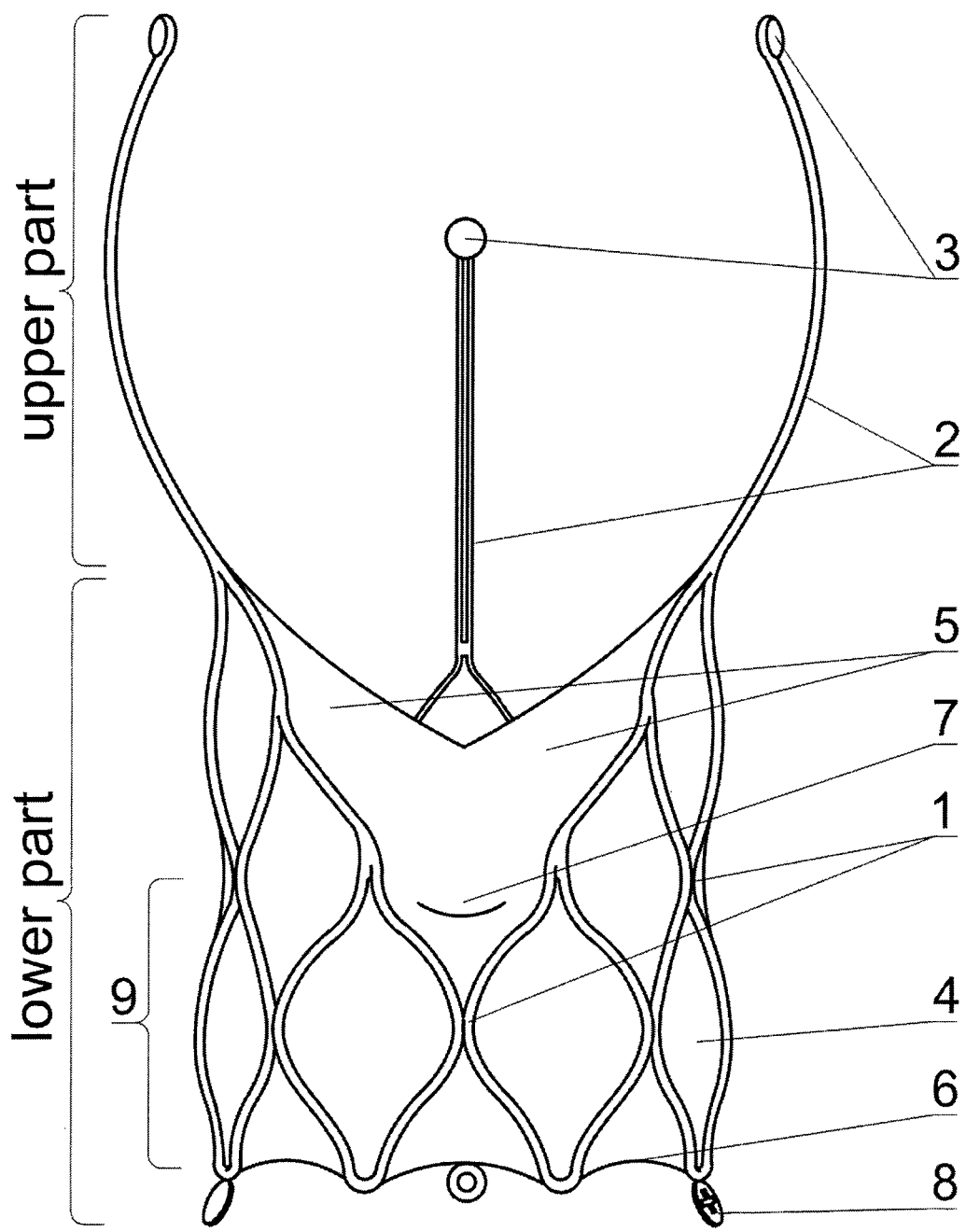
Figure 5:
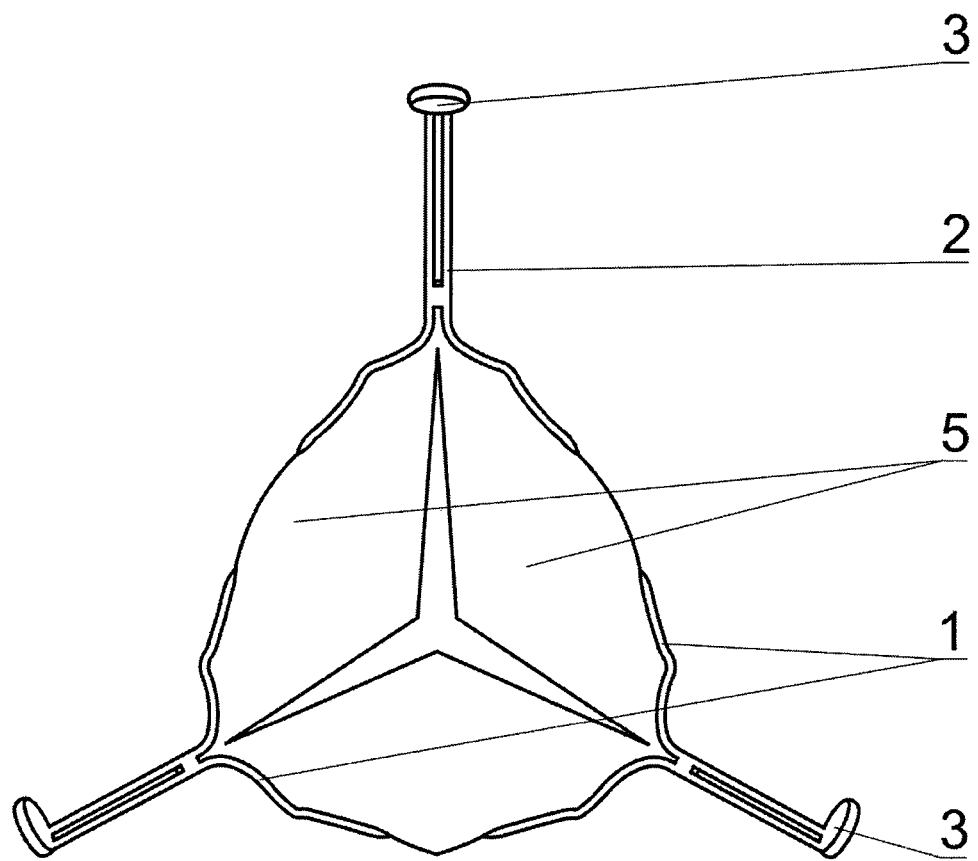
Figure 6:
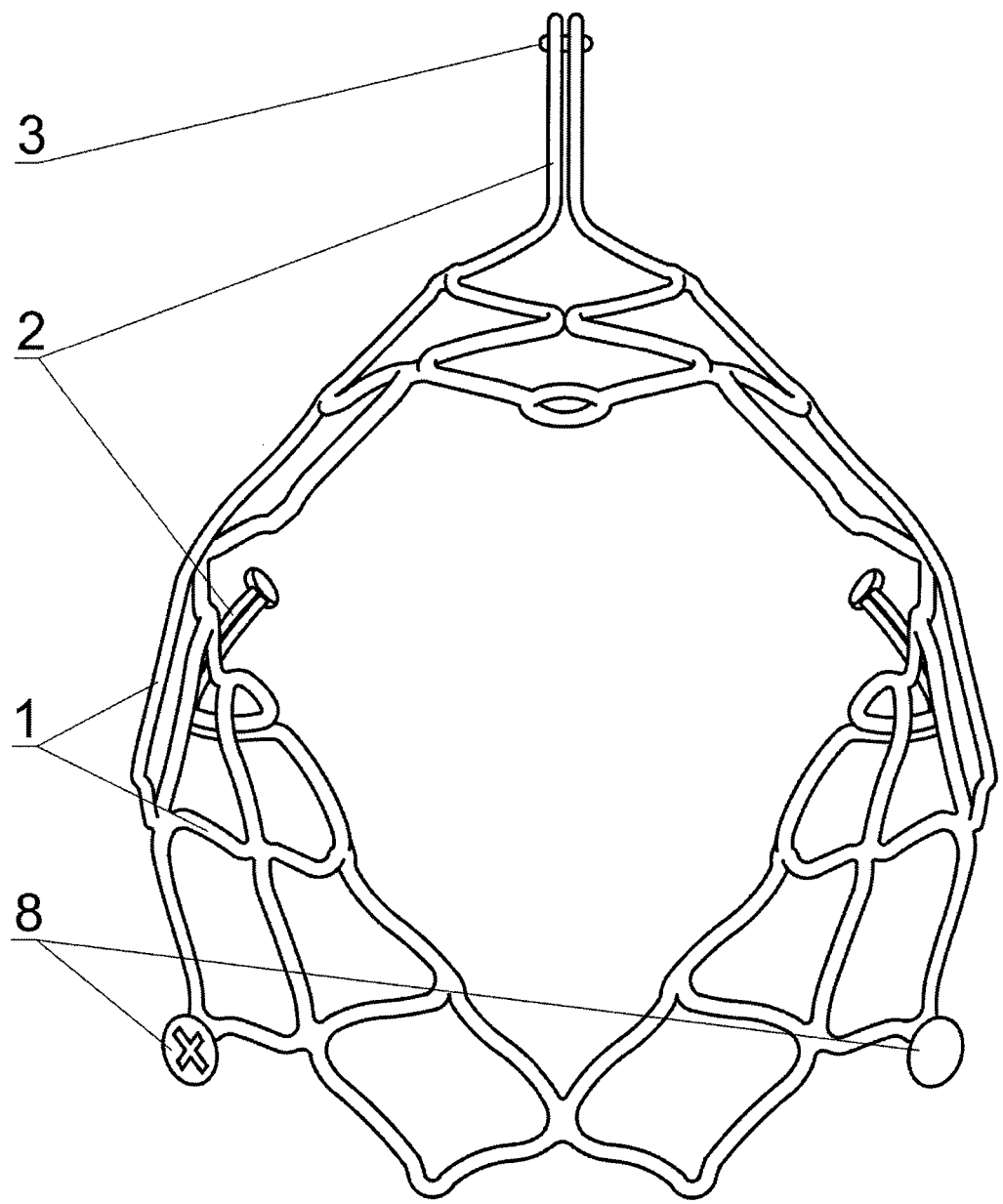

The subject of the invention is shown in the embodiment in drawings, where FIG. 1—shows the side view of the stent of aortic valve with nine rows of holes, FIG. 2—shows the side view of the stent of aortic valve with five rows of holes, FIG. 3—shows the side view of the stent of aortic valve with three rows of holes, with drawn membrane and leaflets of the aortic valve, FIG. 4—shows the side view of the stent of aortic valve with three rows of holes, of slightly different shape with drawn membrane and leaflets of the aortic valve, FIG. 5—shows the top view of the stent with drawn not fully closed leaflets of the aortic valve, FIG. 6—shows the diagonal lower view of the stent with visible lower tags.

The stent of a self-expandable, possible to be repositioned aortic valve implanted transcatheterly provides a flexible framework which consists of two parts: the upper part and the lower part. The lower part is a mesh 1 laid out so that it creates a kind of cylinder wall or almost a cylinder wall on the entire height of the element. Wherein the mesh 1 can be flattened cylinder-shaped or partly funnel-shaped or hourglass-shaped.

Planning a necessary degree of oversizing of an implanted valve in relation to the size (circumference or area) of the patient's aortic valve annulus is possible, in particular in case of a cylinder-shaped stent. This is enabled through earlier determination of the patient's size of aortic valve annulus and known and appropriately matched size of the lower part of the stent.

Oversizing of the valve is the % by which the circumference or surface area of the base of the stent are greater from the circumference or surface area indicated by the patient's aortic valve annulus. Adjustment of those values and use of the stent with appropriately matched oversizing is necessary due to the fact that, in addition to the shape of the stent, it is one of the mechanisms for maintaining the valve in the place in which it was implemented. Oversizing results also in close adjustment of the stent to the patient's aortic annulus after the removal of the delivery system elements.

However, the upper part of the stent consists of derived from the mesh 1 upwards and arranged at equal intervals three arms 2 the height of which is slightly larger than the height of the mesh 1, a bit less than the height of the mesh 1 or equal to its height. The arms 2 are shaped in such a way that together they make up a kind of contour of an oval chalice bowl. The end, peripheral part of each of the arms 2 is usually straight or curved inwards or inclined outwards. At the same time, the whole arms 2 are:
  S-shaped or
  C-shaped or
  straight and
at the same time are:
  pointed straight up or inclined to the middle or
inclined outwards.

The arm 2 can have a single or double structure, i.e. it may consist of a single boom or two juxtaposed with each other, or integrated or at least partly adjacent to each other. When they are made from a material used for the mesh 1 then they can be derived directly from the mesh 1.

The free space between the arms 2 provides easy access after the valve implantation to the patient's coronary arteries from the side of the aorta bulb. At the end of each arm 2 the upper valve tag 3 is placed the shape of which typically resembles a small, low, almost flat cylinder with rounded edges. Equally favorable, it may also have a flat element shape of unique shape which preferably, has characteristic and characterizing it holes or patterns. Therefore it may have a through hole in the middle, and may be, for example, of a spherical disk shape. It may be derived from the arm 2 and may, for example, be formed as a result of curling up the material from which the arm 2 is made or from which the mesh 1 is made. The upper tag 3 allows you to anchor the stent in the delivery system, used for the implantation of the valve. It is an element for fixing the stent to the delivery system, and at the same time its shape provides easy disconnection of the valve from the delivery system at time of the final valve implantation.

The arms 2 designed in such a way with the upper tags 3 of the arms 2 supporting it—ease embedding of the valve in the delivery system and enable holding them by this system in the case of a necessity to reposition the valve.

A sealing membrane 4 is sewn into the described stent or more precisely into its lower part. The membrane is integrated, e.g. sewn at the top with the valve leaflets 5. These elements, i.e. the membrane 4 and leaflets 5 may be made of the same material. While usually the leaflets 5 are made of bovine or porcine pericardium or other biological material or synthetic material. The area between the lower edge of the membrane 6 and the upper edge of the membrane 4 (stretching along the base of the arms 2)—is a zone of sealing and adhesion of the implanted valve to the patient's aortic valve annulus. However, the lower parts 7 of the leaflets may be located, i.e. attached to the membrane 4 at different, preplanned height. It seems that it is more favorable to implant the valve slightly higher over the annulus of the patient's anatomical aortic valve (supra-annularly). Each of the three leaflets 5 of the valve is always sewn between the arms 2 because then when the leaflets 5 of the implanted aortic valve are opposite the leaflets of the patient's aortic valve, the space between the arms 2 will allow free access to the coronary arteries.

The majority of patients has the aortic valve annulus with an oval shape. Then, even if the implanted valve takes an oval shape at the bottom, at the top it has a nearly circular or round shape and functions correctly, i.e. it enables the proper closure of its leaflets 5.

An optimal place for the leaflets 5 to be sewn will be established as a result of the carried out further research and work. It is assumed in the embodiment, that the lower edge 6 of the implanted valve—measured from the base without the lower tags 8, i.e. from the lower tops of mesh holes constituting the lowest, first row 9 of the mesh holes 1—it is distant from the lower edge 7 of the leaflet 5 of the aortic valve preferably by 12 mm. It can be otherwise, the optimal distance of these elements will also be determined in the course of further research and work.

Each upper tag 3 corresponds to the located at the bottom, i.e. on the opposite side and under a given arm 2 lower tag 8. The lower tags 8 are usually placed at the same angle on the outside of the cylindrical or almost cylindrical mesh 1 and are, as they were, its extension. They may be ring-shaped with different fillings, or they are extended and are usually derived from the material used for the mesh 1 or can be made of a different material and only attached to the mesh 1.

It is vital that each lower tag 8 is different from other lower tags 8. They are at the same time visible and recognizable in radiation during x-ray fluoroscopy, (that is, the radiological imaging performed at the time of valve implantation), and owing to this they are helpful in the process of determining and selecting the appropriate valve position. The lower tags 8 allow at the time of implantation for such orientation of the stent in the space obtained by twisting the delivery system so that all the leaflets 5 of the aortic valve are exactly opposite their counterparts, that is, the leaflets of the patient's aortic valve. This later ensures the above described free access—when it is needed—to the coronary arteries through the space between the arms 2 of the stent. The described design allows precise implantation of the stent.

The lower tags 8 are at the same time additional reinforcement and protection of the valve, preventing movement in the direction of the aorta during contraction of the left ventricle of the heart.

The mesh 1 has at least two, preferably three rows of holes, but equally preferable more rows of holes, i.e. 9 or other quantity (as shown for example in FIG. 1 and FIG. 2). The mesh 1 is cylindrically-shaped or almost cylindrically-shaped primarily in that part of the mesh 1 which is the zone of adhesion to the patient's aortic valve annulus, covering at least the lowest, first row 9 of holes.

One row of the mesh 1 may consist of any number of holes, favorably at least nine. Their quantity usually represents a multiple of the figure three.

In the embodiment (FIG. 3)—mesh holes in the lowest, first row 9 have the shape similar to the contour of longitudinal section of a lemon, and the next row of holes have the shape similar to the contour of a drop, whereas the lower tags 8 are extended. However, holes can have any shape to enable the stent to be folded.

Both the mesh 1 and arms 2 derived from it are made of material showing so-called "shape memory effect", ensuring the possibility of folding and expanding of the valve. Such material can be nickel and titanium alloy, for example nitinol. The elements can be made of nitinol wire. The stent also can be a monolithic element made from nitinol tube out of which the whole stent is laser cut, for example. The mesh 1 and similarly arms 2 also can be made from other material.

The developed stent with the membrane 4 sewn thereinto and with separated in its upper part leaflets 5 constitute a valve prepared to be introduced into the heart through the delivery system. Before the valve is delivered, it is compressed to the dimensions allowing putting a cover thereon. However, its implantation is based on that at the time the valve is at the height of the patient's aortic annulus, the cover is being slid. Then the valve expands and is partially implanted which already allows for the functioning of the valve. After establishing and verifying the valve position as a result of:
    conducted echocardiography and/or
    administering contrast to the aorta bulb during aortography and/or in any other way,
    if this position is correct, further sliding of the cover from the stent and final disconnection of the valve from the delivery system is made. In the event of an incorrect valve position it can be repositioned after reapplying the cover on the stent (before its ultimate disconnection). At the beginning of implantation the cover is slid only so that the lower tags 8 are visible.

Today, the vast majority of patients eligible for transcatheter aortic valve implantation is treated with computed tomography test. On the basis of this test it is possible to priorly determine the x-ray tube angles relative to the hemodynamic table on which the patient lies during the valve implantation. If in this position of the x-ray tube three lower tags 8 are visible in firm, intended placement, ensuring correct setting of the leaflets 5 of the aortic valve opposite the patient's valve leaflets—the valve is implanted. That is why, the developed design of the stent in question is so helpful and important for the proper conduct of implantation of the aortic valve.

LIST OF ELEMENTS 1. mesh;
2. arm;
3. upper tag;
4. membrane;
5. leaflet (of valve);
6. lower edge (of membrane);
7. lower part (of leaflet);
8. lower tag;
9. first row (of mesh holes).

The invention claimed is:

1. A stent of aortic valve that has three arms on the upper part and is self-expandable and repositionable, has two parts: the upper part and the lower part, wherein the lower part has a mesh distributed in such a way that it creates a kind of peripheral wall of the element, and the upper part of the stent has three arms derived from the mesh upwards and arranged at equal intervals the height of which is greater than the height of the mesh, slightly less than the height of the mesh or equal to its height, wherein at the end of each arm an upper tag is placed characterized in that each upper tag (3) has its corresponding lower tag (8) located at the bottom of the mesh (1), that is on the opposite side and below the given arm (2), wherein each lower tag (8) is different from others and can be seen with X-rays, allowing planned and precise implantation of the valve and wherein the upper valve tag (3) resembles in shape a spherical disk or small, low, almost flat cylinder with rounded edges or has a shape of a flat element of unique shape or is derived from the arm (2) and constitutes its curvature and additionally has characteristic holes or patterns.

2. The stent of the aortic valve, according to claim 1, characterized in that at least the mesh (1) is made of material showing "shape memory effect" of nickel and titanium alloy, from nitinol and/or made from wire, or constitutes a monolithic element made from tube.

3. The stent of the aortic valve, according to the claim 1, characterized in that the arm (2) has a single or double structure, consisting of a single boom or two juxtaposed with each other, integrated or at least partially adjacent to each other.

4. The stent of the aortic valve, according to claim 1, characterized in that the mesh (1) has at least two, three or nine rows of holes, wherein the holes have the shape similar to the contour of longitudinal section of a lemon or have the shape similar to the contour of a drop.

5. The stent of aortic valve, according to claim 1, wherein the stent has three arms on the upper part and is self-expandable and repositionable, consists of two parts: the upper part and the lower part, wherein the lower part has a mesh distributed in such a way that it creates a kind of peripheral wall of the element, and the upper part of the stent has three arms derived from the mesh upwards and arranged at equal intervals the height of which is greater than the height of the mesh, slightly less than the height of the mesh or equal to its height, wherein at the end of each arm an upper valve tag is placed, characterized in that each upper tag (3) has its corresponding lower tag (8) located at the bottom of the mesh (1), that is on the opposite side and below the given arm (2), and wherein each lower tag (8) is different from others and can be seen with X-rays, allowing planned and precise implantation of the valve and wherein, the upper valve tag (3) resembles in shape a spherical disk or small, low, almost flat cylinder with rounded edges or has a shape of a flat element of unique shape or is derived from the arm (2) and constitutes its curvature and additionally has characteristic holes or patterns.

\* \* \* \* \*